United States Patent [19]
Hsung

[11] Patent Number: 5,301,677
[45] Date of Patent: Apr. 12, 1994

[54] ARRHYTHMIA DETECTOR USING DELTA MODULATED TURNING POINT MORPHOLOGY OF THE ECG WAVE

[75] Inventor: Jean-Cheui Hsung, Shoreview, Minn.

[73] Assignee: Cardiac Pacemakers, Inc., St. Paul, Minn.

[21] Appl. No.: 833,843

[22] Filed: Feb. 6, 1992

[51] Int. Cl.$^5$ .......................................... A61B 5/0402
[52] U.S. Cl. ..................................... 128/705; 128/702
[58] Field of Search ............................... 128/702–705, 128/419 D; 607/5

[56] References Cited

U.S. PATENT DOCUMENTS

| | | | |
|---|---|---|---|
| 4,453,551 | 6/1984 | Anderson et al. | 128/704 |
| 4,552,154 | 11/1985 | Hartlaub | 128/702 |
| 4,679,144 | 7/1987 | Cox et al. | 128/702 |
| 4,925,443 | 5/1990 | Heilman et al. | 128/419 D X |
| 5,014,284 | 5/1991 | Langer et al. | 128/704 |
| 5,058,599 | 10/1991 | Anderson | 128/705 |

Primary Examiner—Lee S. Cohen
Assistant Examiner—Jeffrey R. Jastrzab
Attorney, Agent, or Firm—Keck, Mahin & Cate

[57] ABSTRACT

An arrhythmia detector includes a delta modulator which digitizes the ECG signal and produces a serial digital signal that represents the input ECG signal. A microprocessor classifies the signal as having no slope, positive slope, or negative slope. A finite state machine model in the microprocessor uses the positive slope, negative slope, or no slope information to determine the number of times an isoelectric line segment is present in the ECG signal. By accumulating the line-counts or number of line segments over a two-second period, a determination can be made whether the ECG signal has been in isoelectric line less than a threshold. For two out of three 2 second periods, if the percentage of isoelectric time is less than the ventricular fibrillation threshold then a ventricular fibrillation signal can be generated. For ventricular tachycardia verses supraventricular tachycardia discrimination, a second threshold which relates to the average heart rate observed in a linear formula LC(TH)=b−a*(rate)/30 can be used. If the isoelectric line-count is less than the LC(TH), then VT is declared. The regression coefficient a and b can be found by measuring the line-count and rate pairs in 2 second periods during normal sinus rhythm in periodic basis, for example, 10 data pairs every hour. The delta modulator uses a comparator which receives the ECG signal and a tracking signal to output a series of binary digits. A digital-to-analog converter generates the tracking signal.

18 Claims, 11 Drawing Sheets

FIG. 1A

NORMAL SINUS RHYTHM

VENTRICULAR TACHYCARDIA

FIG. 1D

ALMOST ALL SLOPES

VENTRICULAR FIBRILLATION

| INPUT | | SOURCE STATE | | | | | | | | | | |
|---|---|---|---|---|---|---|---|---|---|---|---|---|
| | | 0 | 1 | 2 | 3 | 4 | 5 | 6 | 7 | 8 | 9 | 10 |
| 1 UPPER | DESTINATION STATE LINECOUNT | 1 | 2 | 2 | 1 | 2 | 0 +2 | 0 +2 | 10 | 0 +3 | 10 | 2 |
| 0 MIDDLE | DESTINATION STATE LINECOUNT | 0 | 3 +1 | 4 | 0 | 0 | 9 +3 | 8 +2 | 9 | 0 | 0 +3 | 4 +2 |
| −1 LOWER | DESTINATION STATE LINECOUNT | 6 | 0 +2 | 5 | 0 +3 | 5 | 7 | 7 | 7 | 6 | 7 | 0 +2 |

ARRHYTHMIA DETECTOR USING DELTA MODULATED TURNING POINT MORPHOLOGY OF THE ECG WAVE

BACKGROUND OF THE INVENTION

The present invention relates to a detector for analyzing the condition of the heart and is used in conjunction with a device capable of electrically stimulating a heart experiencing ventricular fibrillation, ventricular tachycardia, supraventricular tachycardia, or other arrhythmias. Specifically, the present invention relates to a detector capable of discriminating ventricular fibrillation (VF), polymorphoric ventricular tachycardia (PVT) from other arrhythmias of the heart and discriminating ventricular tachycardia (VT) from tachycardia of supraventricular origin. The present invention also relates to a unique delta modulator that operates on the ECG signal.

OBJECTS OF THE INVENTION

It is an object of the present invention to identify an arrhythmic heart condition by analyzing the waveform (morphology) of an electrocardiogram (ECG) signal obtained from the heart.

It is another object of the present invention to analyze a digital representation of the ECG signal and apply a waveform analysis on that digital signal.

It is a further object of the present invention to utilize a delta modulated representation of the ECG signal and further identify isoelectric segments of the ECG signal based upon the delta modulated representation thereof.

It is another object of the present invention to detect fibrillation and also detect ventricular tachycardia by comparing the isoelectric line segments against two thresholds.

It is an additional object of the present invention to establish a rate dependent tachycardia threshold by monitoring the rate and morphology of the heart both in normal condition and in tachyarrhythmia.

It is another object of the present invention to utilize a unique delta modulator that includes a digital-to-analog converter and an up/down counter which digitally integrates an input signal, and which further incorporates an over-limit feature in order to accommodate an input signal which exceeds the dynamic range limits of the digital-to-analog converter.

It is an additional object of the present invention to provide a delta modulator that is completely drift free and which employs a substantially error-free integrator.

It is a further object of this invention to provide an arrhythmia detection system for measuring slew rate of an ECG signal, and including software to decide whether the ECG signal is typical of ventricular fibrillation, ventricular tachycardia, or other arrhythmias.

Another object of the present invention is to provide a toggled output for the delta modulator when the dynamic range limit of the digital-to-analog converter is exceeded in order to produce a signal which can be readily recognized.

SUMMARY OF THE INVENTION

The arrhythmia detector includes a delta modulator which digitizes the ECG signal and produces a representative serial digital signal. The serial digital signal is loaded as an 8-bit digital word into an 8-bit register, and a microprocessor counts the number of zeros in the 8-bit digital word in order to classify the signal as having no slope, positive slope, or negative slope. The definitions are established so that if more than four zeros occur, the slope is positive; if less than four zeros occur, the slope is negative; and if exactly four zeros occur, there is no slope. The microprocessor utilizes a finite state machine to determine the number of times an isoelectric line segment is present in the ECG signal based upon the series of positive (+) slope, negative (−) slope, or no slope signals. Basically, the finite state machine determines, based upon the previous state and based upon the current positive/negative or no slope signals, what the next state will be. During certain transitions between states, a line-count increment is assigned to the transition. By accumulating the line-count over a two-second period, and comparing it with two thresholds, determinations can be made on whether the ECG signal is indicative of a ventricular fibrillation, a ventricular tachycardia or supraventricular tachycardia.

This turning point morphology analysis technique is not expected to be used alone but, rather, used in conjunction with a detected heart rate signal to determine the presence of fibrillation and/or ventricular tachycardia. One line-count threshold is designed to discriminate between ventricular fibrillation and monomorphic VT and typically used between the rate zone of 150 bpm to 200 bpm. If the line-count accumulated within the two-second period is less than or equal to the first threshold then the period is considered as a condition called Fibrillation Met (Fib-Met). It takes two out of three two-second periods of the Fib-Met condition to generate a fibrillation detected condition for invoking defibrillation therapy. The second threshold is targeted at distinguishing between ventricular tachycardia and supraventricular tachycardia and it is typically applied in the rate zone 110 bpm to 150 bpm. The threshold can be decided on a rate dependent fashion by measuring the line-count and average rate in two-second periods with the ECG signal indicating normal sinus rhythm.

Using a first order approximation, a regression relation (line-count) $LC = b - a^*rate$ can be assumed for tachycardia from a supraventricular tachycardia origin, and the regression coefficients a and b obtained from the measured data pairs. With the suspected high rate in the rate zone 110 bpm and 150 bpm, and the measured coefficients a and b, a threshold LC(TH) for the line-count can be generated. When the line-count is less than the threshold, the rhythm is declared to be ventricular tachycardia and anti-tachy therapy can be invoked. Otherwise, the rhythm is judged to be from supraventricular origin, and no anti-tachy therapy will be invoked.

The delta modulator of the present invention includes a comparator that receives the ECG signal at one input and a tracking signal at the other input. A digital-to-analog converter (herein a D/A converter) generates the tracking signal for the comparator. An up/down counter supplies the digital signal to the D/A converter. The up/down counter has an up/down control input that is coupled to the output of the comparator. The up/down counter counts clock signals applied to its clock input. Therefore, when the ECG signal level is above the tracking signal level, that is, the analog version of the count in the counter, the comparator's output goes high, and the counter begins counting up. When the ECG signal level is lower than the tracking signal level, the comparator's output goes low, and the counter begins to count down. Therefore, the combination of the D/A converter and the up/down counter digitally integrate the ECG signal. The output of the comparator is a delta modulated signal.

The delta modulator of the present invention may also include an over-limit control that toggles the output of the comparator when the counter reaches its maximum or minimum count value. The counter has a Carry signal (for excessive counts) and a Not Borrow signal (for less-than-zero counts). These two signals are fed into a logic circuit that toggles the output based thereupon at the clock pulse rate.

The above and other objects and advantages of the present invention will become more readily apparent in the following description taken in conjunction with the accompanying drawings.

DETAILED DESCRIPTION OF THE DRAWINGS

The present invention relates to an arrhythmia detector that can be used in an implantable cardioverter or an external automatic defibrillator or cardioverter. Particularly, the detector comprises a ventricular fibrillation and ventricular tachyarrhythmia detection algorithm that analyzes the shape of the ECG waveform or morphology of the cardiac signal obtained from the heart. The ECG signal can be obtained from intracardiac leads, surface leads or from an external sensory device coupled to an external automatic defibrillator.

The present invention also relates to a unique delta modulator structure that utilizes an up/down counter and a digital-to-analog converter.

As for the arrhythmia detector, the principle of fibrillation detection is based on the premise that the fibrillation waveform, as obtained from both surface leads on intracardiac leads (e.g., a widely placed spring to a patch or patch to patch), is somewhat sinusoidal in nature. The frequency of the quasi-sinusoidal wave is typically in the range of 2 to 9 Hz. Compared with ventricular tachycardia, supraventricular tachycardia and normal sinus rhythm waveforms, a sinusoidal ventricular fibrillation waveform has fewer isoelectric segments. Therefore, a calculation of the amount of time the overall ECG waveform is an isoelectric line is an indication of ventricular fibrillation.

FIGS. 1A-1D show a normal sinus rhythm (NSR) ECG waveform wherein the heart rate is 75 bpm (FIG. 1A), a supraventricular tachycardia (FIG. 1B) and ventricular tachycardia (FIG. 1C) both with rate of 150 bpm. A VF waveform (shown in FIG. 1D) is comprised almost entirely of sloped line segments. As shown, a normal ECG is comprised of primarily an isoelectric line except for the QRS complex. The threshold between supraventricular tachycardia and ventricular tachycardia can be decided based on a model that the line-count from NSR and supraventricular tachycardia can be related by (line-count) $LC = b - a*rate$, wherein line-count from ventricular tachycardia is less than the supraventricular tachycardia with equal rate. Therefore, by measuring the line-count from waveform of NSR in various rates, the regression coefficients a, b can be decided, and the threshold between supraventricular tachycardia and ventricular tachycardia can be projected from the coefficients and the measured rate from the arrhythmia in question. If the line-count is less than the threshold, the rhythm in question is classified as ventricular tachycardia. Otherwise, it is classified as tachycardia with supraventricular origin.

In one embodiment of the present invention, the ECG signal is fed to a delta modulator (described later with respect to FIGS. 11 and 12), and the delta modulator produces a serial digital output. This serial data is loaded into an 8-bit register, and the contents of the register are analyzed by a microprocessor-based control system. The microprocessor-based control system in one embodiment includes a microprocessor, a random access memory for storing variables and other items of information, and a read-only memory for storing software programs and routines which are called up by the microprocessor to operate on the various inputs supplied thereto.

Generally, the microprocessor samples the 8-bit register holding the delta modulated ECG signal at 1 KHz sampling rate. The step size of the delta modulator is 1/16 from the base line to maximum amplitude of the ECG signal or 32 steps peak-to-peak of the ECG signal. This is a 5-bit resolution for the delta modulator. Every eight milliseconds (7.8125 msec to be precise), the microprocessor counts the number of zeros in the 8-bit data word in the register in order to determine whether the slope of the delta modulated signal is up (positive), zero (no change), or down (negative). If the number of zeros is greater than four, the slope is up (+1); if the number of zeros is equal to four, there is "no slope" (0); if the number of zeros is less than four, the slope is down (−1).

Thereafter, the contextual or waveform relationship of these clusters (the 8-bit delta modulated data word) is analyzed using a finite state machine algorithm. The finite state computational model separates the clusters into flat line segments and sloped line segments, based upon the threshold of 16/125 step/ms. This corresponds to the situation in which, if the slew rate is greater than or equal to a linear monotonic rate of change from the isoelectrical line to the maximum amplitude in 125 msec, then the segments in question are defined as slope. Otherwise the segments in question are defined as a flat line. The turning points of the sloped segments can be followed by the finite state algorithm, and line-counts increments are assigned to certain state transitions, as defined by the finite state machine algorithm. The line-counts, indicative of the number of isoelectric line segments in the ECG waveform, are added up over the 2 second period, and a determination is made whether the amount of time the ECG signal is an isoelectric line is less than a predetermined threshold. If the time in isoelectric line is less than the VT/VF threshold, this two-second segment is considered Fib-Met. It takes two out of three two-second segments satisfying this condition to invoke a fibrillation detected signal.

Figure 1A:
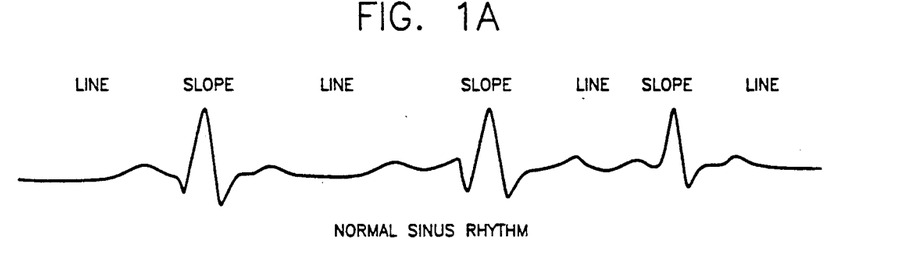
FIGS. 1A-1D illustrate ECG waveforms from normal sinus rhythm, supraventricular tachycardia, ventricular tachycardia and ventricular fibrillation.
Figure 1B:
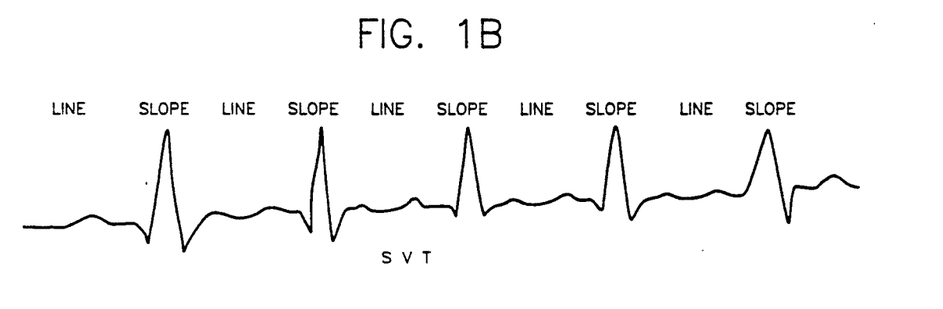
Figure 1C:
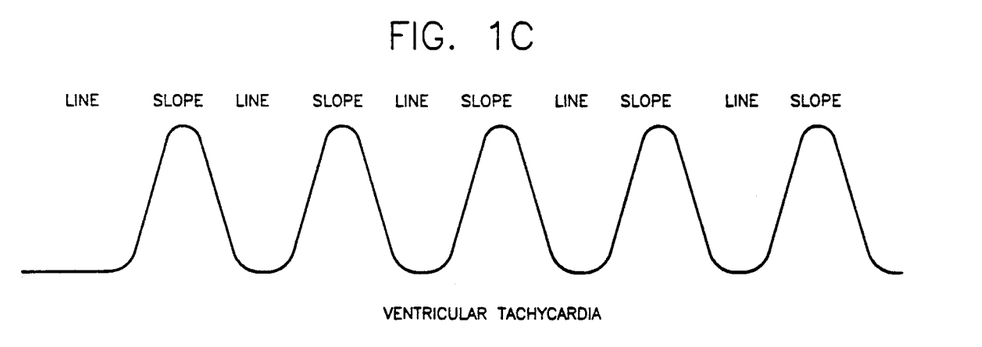
Figure 1D:
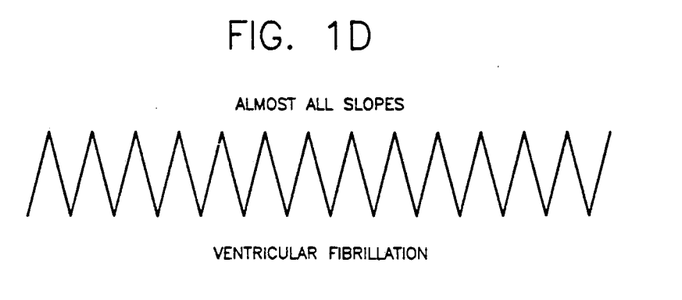
Figure 2:
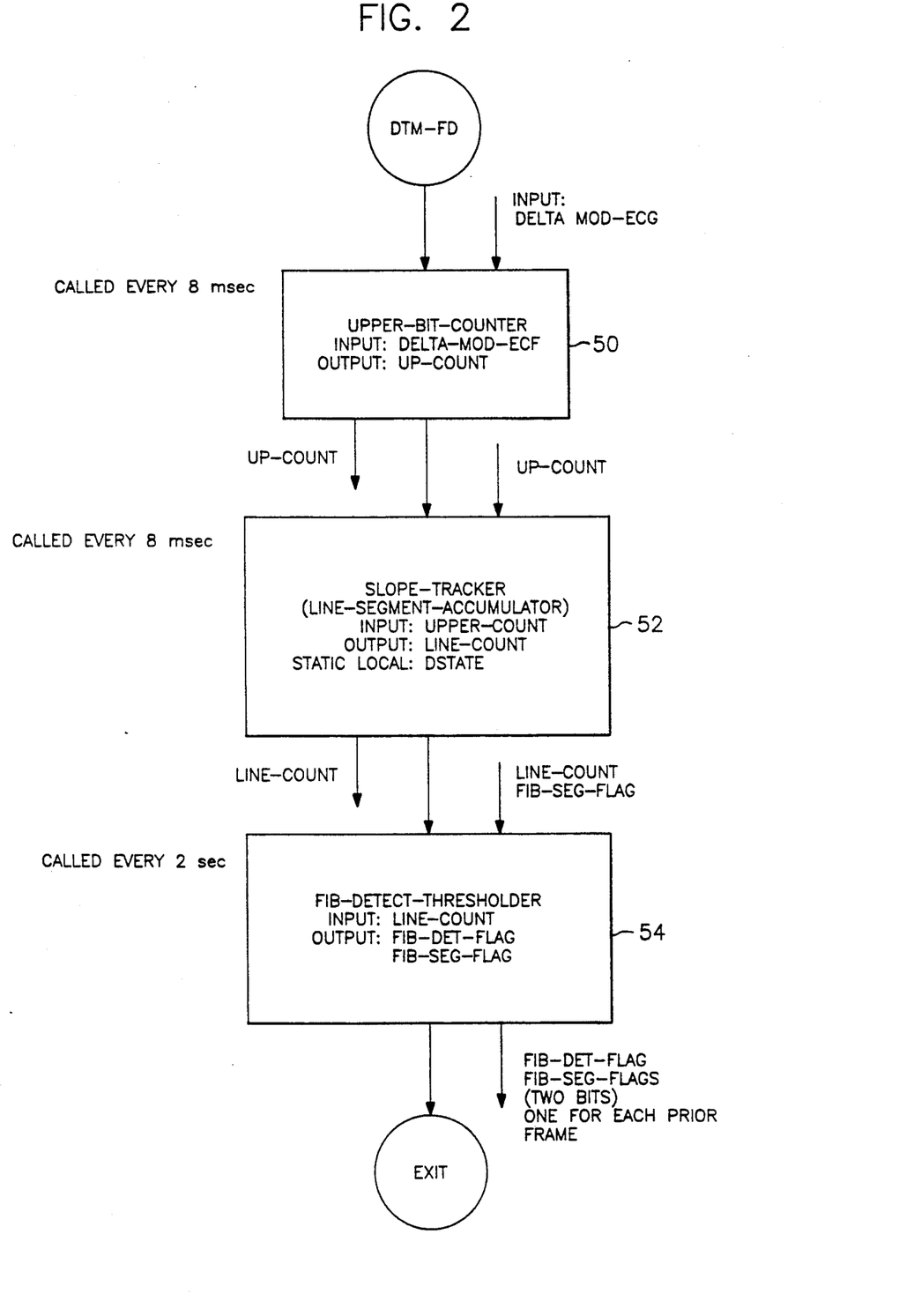
FIG. 2 is a data flow diagram for the arrhythmia detector in accordance with the principles of the present invention.

FIG. 2 shows a data flow diagram of the present invention. DMT-FD is a label for the delta modulated turning point morphology routine. Block 50 represents analysis of the upper-bit-counter and is called every 8 msecs. The input into block 50 is the delta modulated ECG signal. An upper bit counter is utilized to determine the number of zeros in the 8-bit delta modulated signal (stored as an eight bit data word called delta-mod-ECG) and hence positive/negative or no slope of the signal. The output is the up-count.

Block 52 represents the slope tracker which receives the up-count and accumulates the line segments. The output of block 52 is a line-count and a state variable of the finite state machine called "dstate". Block 54 is the fibrillation detection thresholder which receives the line-count and the fibrillation segment flag (fib-seg-flag). Block 54 is called every two seconds and outputs a fibrillation detection flag (fib-det-flag) and a fibrillation segment flag (fib-seg-flag) that is indicative of the previous two thresholding tests. The fib-seg-flag is two bits wherein each bit represents a prior frame's threshold result.

Figure 3:
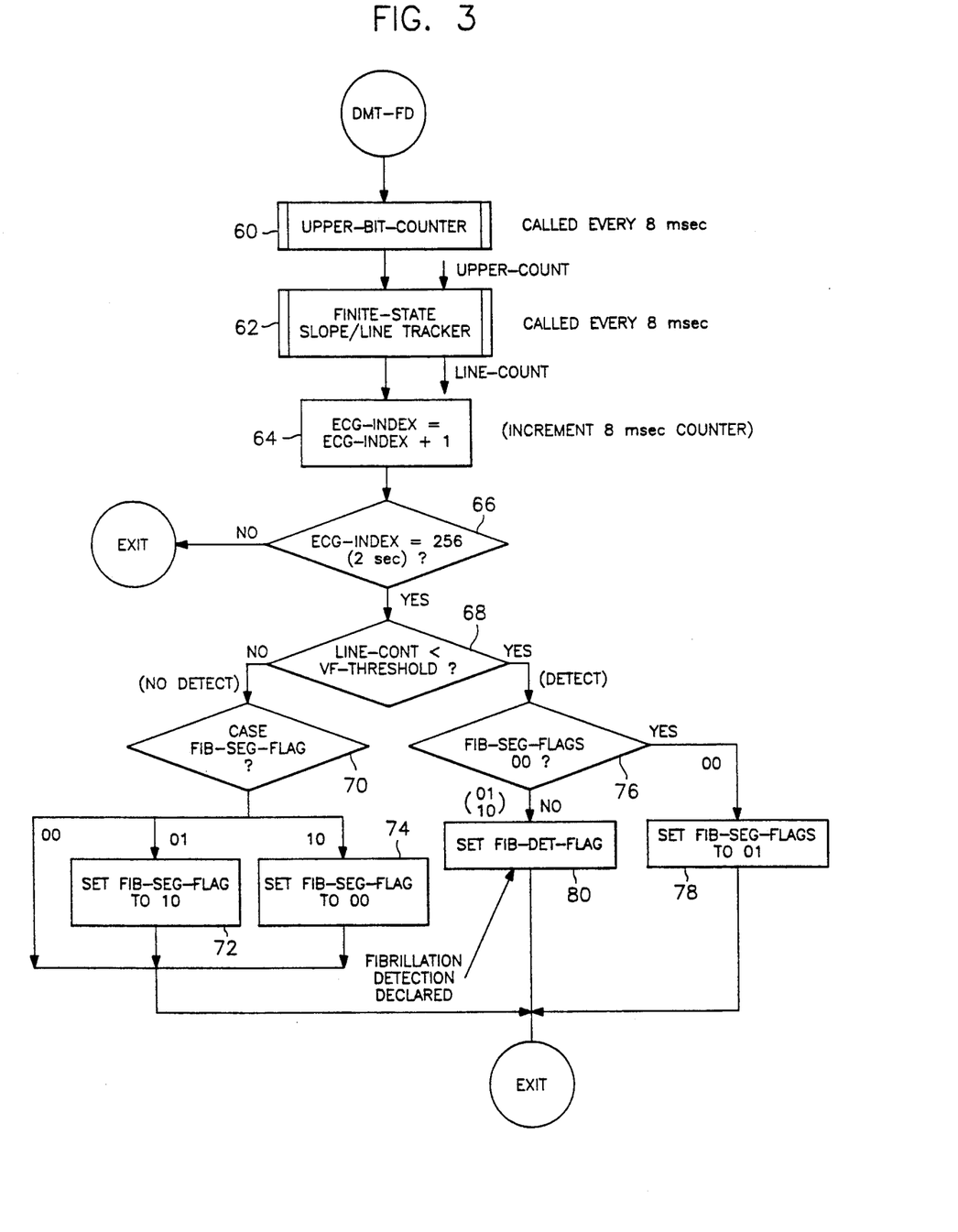
FIG. 3 is a flowchart for the arrhythmia detector in accordance with the principles of the present invention.

FIG. 3 illustrates, in greater detail, the flowchart for the delta modulated turning point morphology routine (DTM-FD). Before this routine is called, various items are initialized to zero, for example, the ECG-INDEX, line-count, and dstate are all set to zero, and the fib-det-flag and fib-seg-flags are cleared. In step 60, the bits of the register DMT-MOD are examined to determine the number of zeros in this eight bit register. In step 62, a finite state machine is invoked to compare the status of the current segment with previous segments. Finally, in steps 64-80, certain thresholds are applied to output generated by the finite state machine of step 62 to determine the type of cardiac rhythm occurring.

Figure 4:
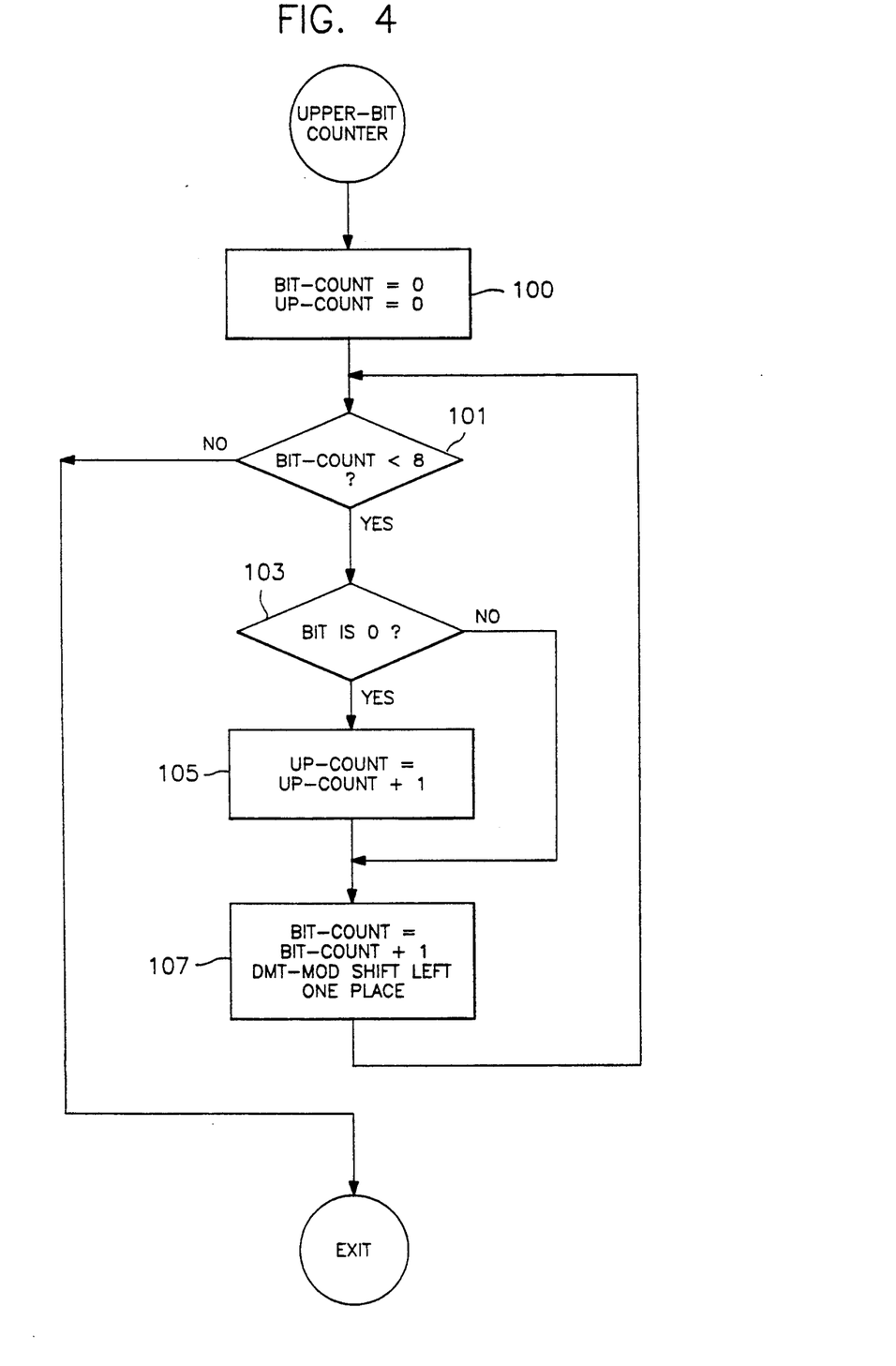
FIG. 4 is a flowchart of the upper bit counter routine.

FIG. 4 shows the detailed flowchart for upper bit counter routine 60. In step 100, the bit-count is set to zero, and the up-count is set to zero. Decision block 101 determines whether the bit-count is less than eight; and, if it is not less than eight, the routine is exited until at next examination bit-count is less than eight. If the bit-count is less than eight, decision block 103 determines whether bit 7 is equal to zero. The 8-bit data word (delta-mod-ECG) is loaded into a hardware shift register (DMT-MOD), and it is that register that is being read. The 8-bit word has bits 0, 1, 2, 3, 4, 5, 6, and 7. Steps 103 and 105 determine how many of the bits in the 8-bit register are equal to zero, and the value of up-count is equal to the number of zeros. Each time a test is made on a bit, the bit-count value is incremented in step 107, and the shift register DMT-MOD is shifted one place to the left. When all the bits have been read from the register, the routine is exited. Although up-count can have a value anywhere from 0 to 8 (0 if no zeros have been found or 8 if eight zeros have been found), for purposes of understanding the invention, if up-count is greater than four, a positive slope is identified; if up-count is equal to four, zero slope is noted; and, if up-count is less than four, a negative slope is recognized for this eight msec data as a whole.

Returning back to FIG. 3, the up-count value is supplied to the finite state slope/line tracker subroutine in step 62. Step 62 is a finite state machine algorithm which separates series of slope signals, each slope representative of an 8 msec cluster of delta modulated signals, into line segments and slope segments and assigns line-count increments to certain turning points or transitions.

Figure 5:
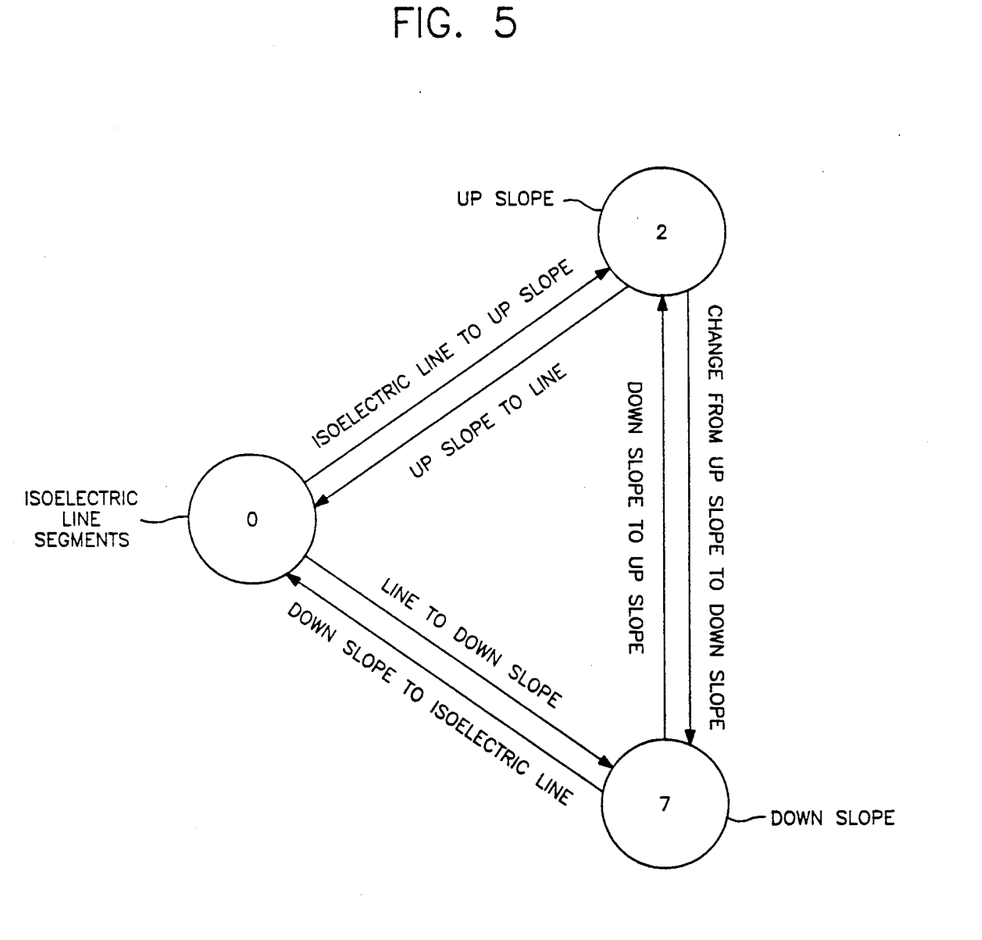
FIG. 5 is a condensed version of the state diagram for the present invention.

A simplified finite state machine algorithm is shown in FIG. 5. The 0 state (dstate=0) defines an isoelectric line segment. Dstate is initialized to 0. If no slope is detected at the first 8 msec interval, the algorithm provides that the state remains at 0. If +1 or positive slopes are detected, the algorithm provides that state 2 is entered. If from state 0 negative slopes (−1) are detected, the state changes from 0 to 7. If from state 7 positive slopes are noted, the state changes to 2, etc., according to the finite state algorithm. Line count increments can be assigned to particular transitions between states.

Figure 6:
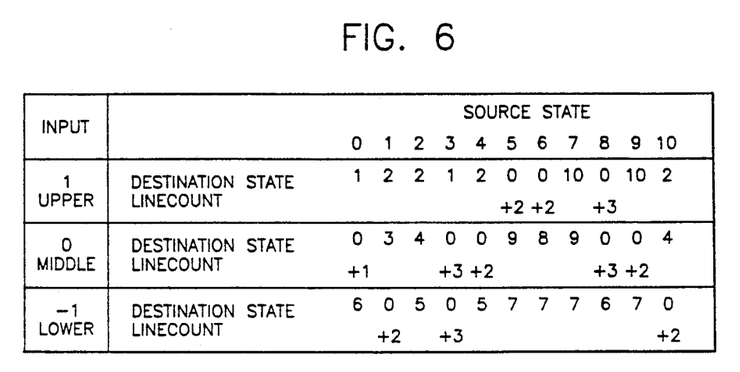
FIG. 6 is a tabular representation of the finite state machine or state diagram.
Figure 7:
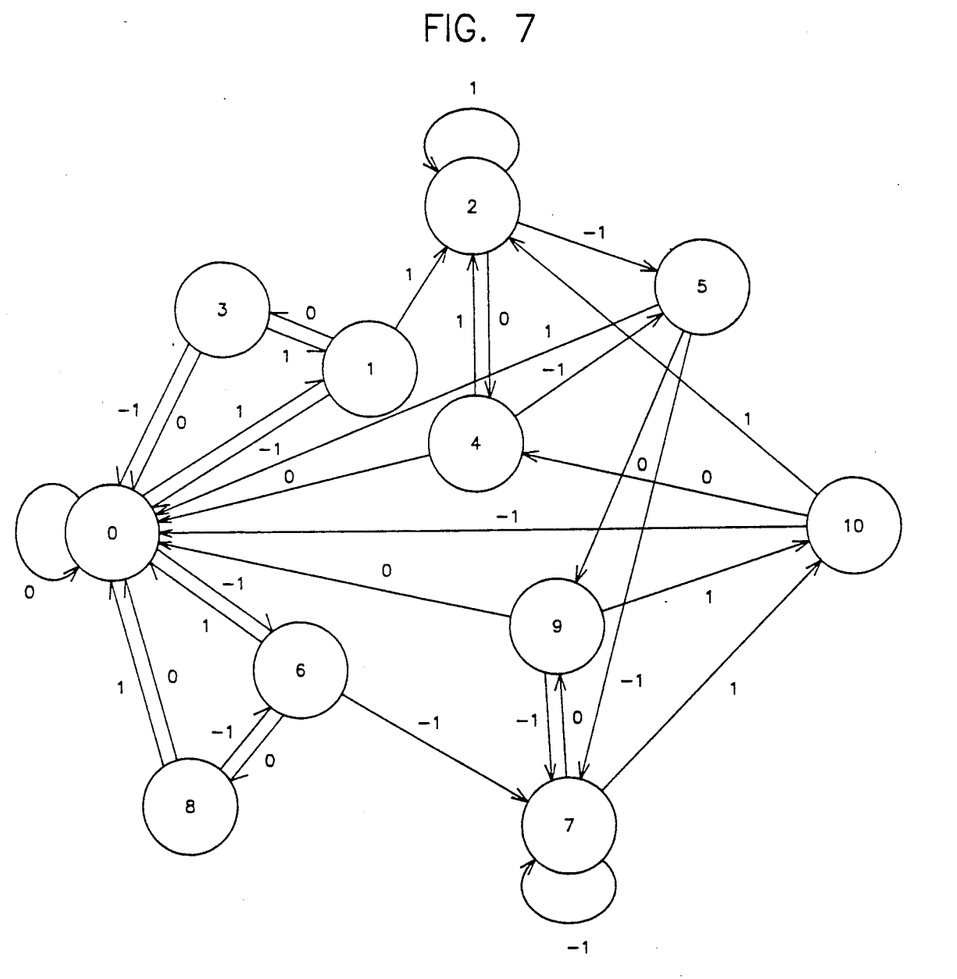
FIG. 7 is a graphical representation of the finite state machine.

FIGS. 6 and 7 represent the detailed finite state machine algorithm in accordance with the preferred embodiment of the present invention. FIG. 6 is a tabular representation of the finite state algorithm which comprises a look-up table for the destination states and the possible line-count increments accompanying state transitions to dstate 0, whereas FIG. 7 is a state diagram graphical representation of the same algorithm. In these figures, 11 states numbered 0 to 10 are represented. For certain state transitions, for example, from state 5 or state 6 in the presence of a positive input slope (1) a state transition to state 0 will occur and the line-count is incremented by 2. From state 1 or 10, a negative input slope (−1) will cause a state transition to 0 with a line-count increment of 2. Therefore, by accumulating the line-counts and maintaining a record of the source state (dstate), certain transitions to dstate 0 which are indicative of the isoelectric line segments are assigned line-count increments. It should be noted that a significant transition occurs even when the dstate does not change numerically. For example, the state transition from dstate 0 to dstate 0 in the presence of zero slope is assigned a line-count increment of 1.

By analyzing the morphology of waveshape of the ECG signal, a determination can be made as to what weight or what incremental value should be assigned to the line-count for a particular state transition.

States 0, 2, and 7 have special meanings and, as such, are termed primary states. State 0 is the primary state for line segments that have no slope. State 2 is the primary state for upward sloping segments. State 7 is the primary state for downward sloping segments.

Figure 8:
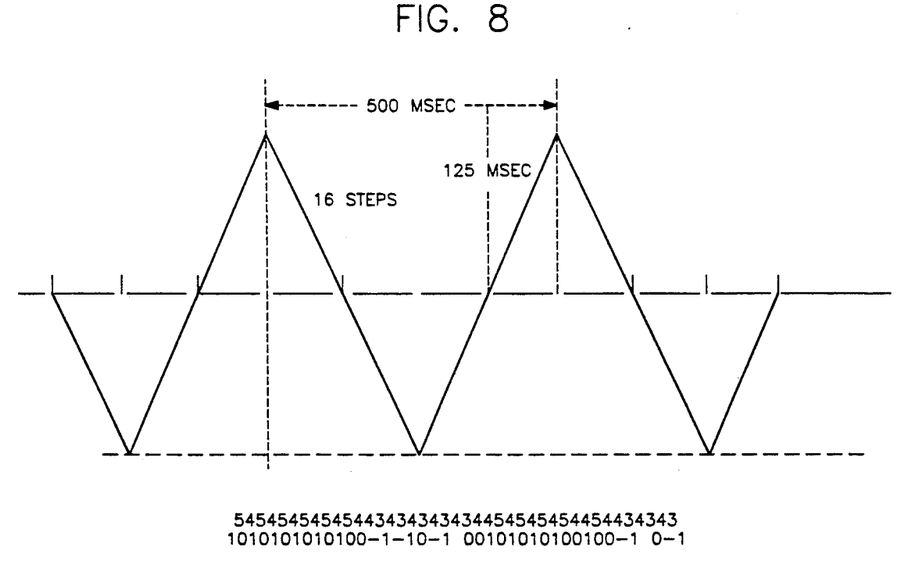
FIG. 8 illustrates a thresholding waveform incorporated into the finite state machine illustrated by FIGS. 6 and 7.

The transition from state 0 (the ECG in isoelectric line) to state 2, requires at least two upward transitions. This corresponds to an average slope of at least 4 steps in 16 msec segment from a flat line segment. States 1 and 3, between states 0 and 2, and the transition rules that attach to them, are designed to establish a thresholding waveform. A direct state transition for state 0 to 1 to 2 in two data samples corresponds to a slope of at least 4 steps in 16 msec or from isoelectric line to maximum amplitude in 64 msec. Therefore, if slope criteria is shallower than that, some intermediate states are needed. States 1 and 3 between 0 and 2, (similarly states 6 and 8 between 0 and 7) and the transition rules that attached to them are designed to establish a threshold such that ECG segments with slew rate greater than or equal to a linear monotonic rate of change from baseline to maximum amplitude in 125 msec will be classified as slope segments; otherwise they will be classified as flat line segments. This is accomplished by distinguishing line segments with a pattern 101010101 or -10-10-1 as slope and any segments with shallower slew rate will be classified as line segments. This thresholding waveform is a 2 HZ sawtooth waveform as illustrated in FIG. 8. When a transition back to state 0 occurs (including 0 to 0 transition) line-count will be incremented by 1, 2 or 3.

Figure 9:
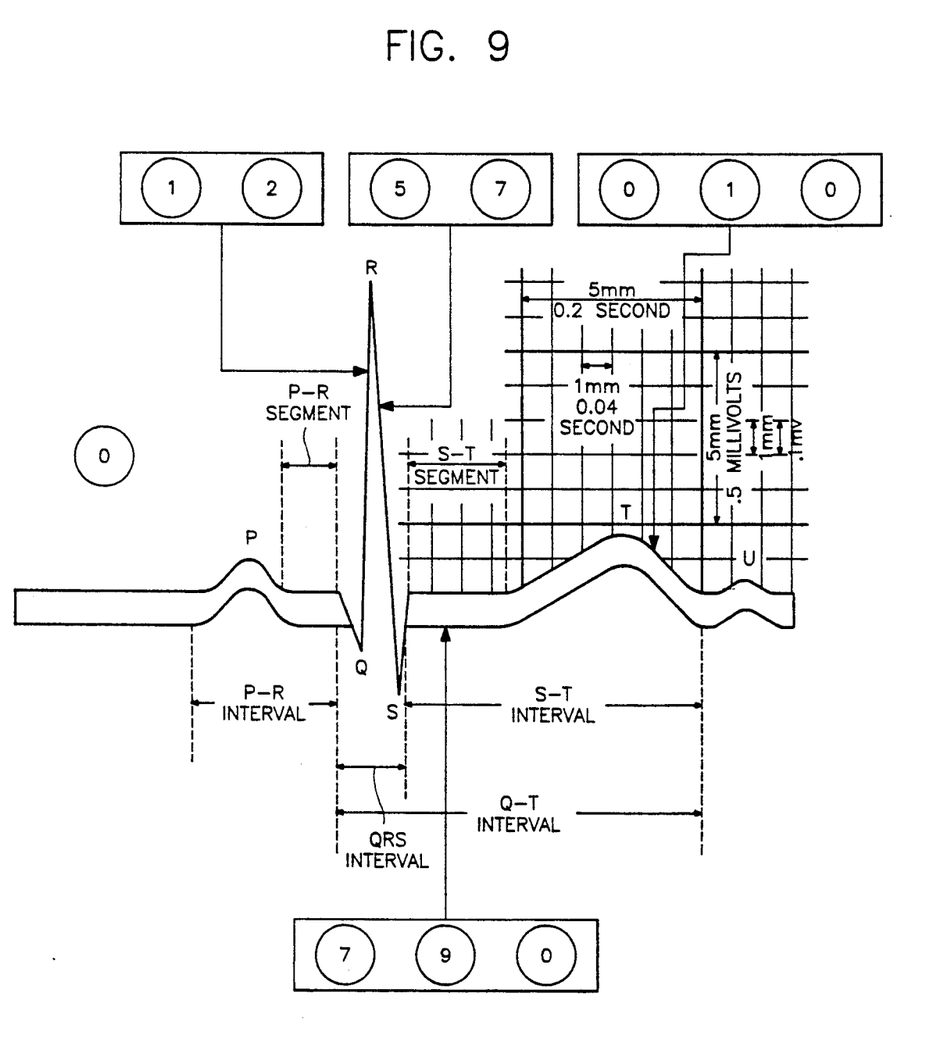
FIG. 9 illustrates an ordinary ECG as it is analyzed by the finite state machine illustrated by FIGS. 6 and 7.

Referring to FIG. 9, the analysis of an ordinary ECG is illustrated. The QRS complex is seen as having slopes steeper than that of the threshold waveform illustrated in FIG. 8. Specifically, the QRS complex has a corresponding dstate sequence of 1, 2, 5, 7. The thresholding waveform assists in discriminating slope segments from flat line segments by affecting the value of line-count in dstate transitions.

Returning to the flowchart shown in FIG. 3, a line-count is generated from the finite state machine in step 62. In step 64, the ECG-INDEX is incremented by 1. In step 66, a determination is made whether ECG-INDEX is equal to 256. When the ECG-INDEX is equal to 256, two seconds have passed, and the first threshold decision is made in step 68. In step 68, a determination is made whether the line-count is less than the VF-threshold which indicates the percentage of time the ECG is in flat line segments within this 2 seconds. From empirical studies of about 90 ECG recordings from internal leads, the threshold is set to be between 35 to 40%. It is expected to be a programmable parameter adjustable to individual patients.

If decision step 68 determines that the number of accumulated line-counts exceeds the threshold during the two-second period, the NO branch is taken to decision step, which determines which step is taken dependent upon the 2-bit value of the flag. Each bit of the flag represents a previous state of the flag. 00 represents that the flag was not activated during each of the prior two-second periods. 01 indicates that the flag was set in the last two-second period but not in the prior two-second period. 10 indicates that the flag was set in the earlier two-second period, but not in the immediately preceding two-second cycle. Steps 72 and 74 which set the fib-seg-flag to 10 if the flag was previously 01 and to 00 if the flag was previously 10 will be executed if the current segment does not exceed the VF-threshold. This subroutine in combination with the YES branch steps from step 68 is basically a voting scheme which determines in two out of the last three 2 second segments whether a fibrillation or an arrhythmia has been detected.

If YES branch is taken from decision block 68, a decision is made in step 76 whether the fib-seg-flag is 00. If YES, step 78 sets the fib-seg-flag to 01, and the routine is exited. If the decision from step 76 is such that the fib-seg-flag is not 00, then in step 80 both the most significant and least significant bits of the fib-det-flag are set which indicates that fibrillation or arrhythmia has been detected and declared, and that the most recent 2 second segment is FIB-MET. In step 80, it does not matter whether the arrhythmia was detected in the immediately preceding two-second interval (fib-seg-flag=01) or whether the arrhythmia was detected in the earlier two-second interval (fib-seg-flag=10), since the YES from step 68 indicates that two out of the three segments are FIB-MET in either case (11 or 01). At that point, the routine is exited.

Alternatively, for surface ECG's sampled at 256 samples/second, delta modulation can be performed on 4 msec data from two samples points. Contextual relations of the cluster of two points can also be followed using a similar finite state scheme.

For ventricular tachycardia detection, in contrast to ventricular fibrillation detection, there is no particular reason to fix the slope threshold for ventricular tachycardia detection to 16 steps from baseline to maximum amplitude within 125 msec. However, for simplification, it is reasonable not to change the slope thresholding for ventricular tachycardia detection but rather to change the percentage in isoelectric line threshold. For normal sinus rhythm, isoelectric line/percentage is approximately 85 percent during one cardiac cycle; for ventricular arrhythmias, the percentage is approximately 55 percent; and for supraventricular tachycardia (SVT), the percentage is around 65 to 75 percent. The main problem of poor specificity for ventricular tachycardia detection based on rate criteria alone is due to the overlap in rate of VT with that of sinus tachycardia or supraventricular tachycardia. Therefore, another thresholding technique is utilized in a preferred embodiment of the present invention.

This further technique is based on the assumption that the morphology of individual QRS complexes or "the effective width" of supraventricular tachycardia versus normal sinus rhythm will be similar for most individual patients. Therefore, the line-count derived from tachycardia with a supraventricular origin can be related to line-counts (LC) and rates in normal sinus rhythm as a linear formula LC=b−a*rate. However, the QRS complex of the ventricular tachycardia will have a different morphology, typically wider. Therefore, by collecting baseline morphology information periodically during normal sinus rhythm, and measuring the rate at the same time, a ventricular tachycardia versus supraventricular tachycardia threshold is generated on a rate dependent basis.

Figure 10:
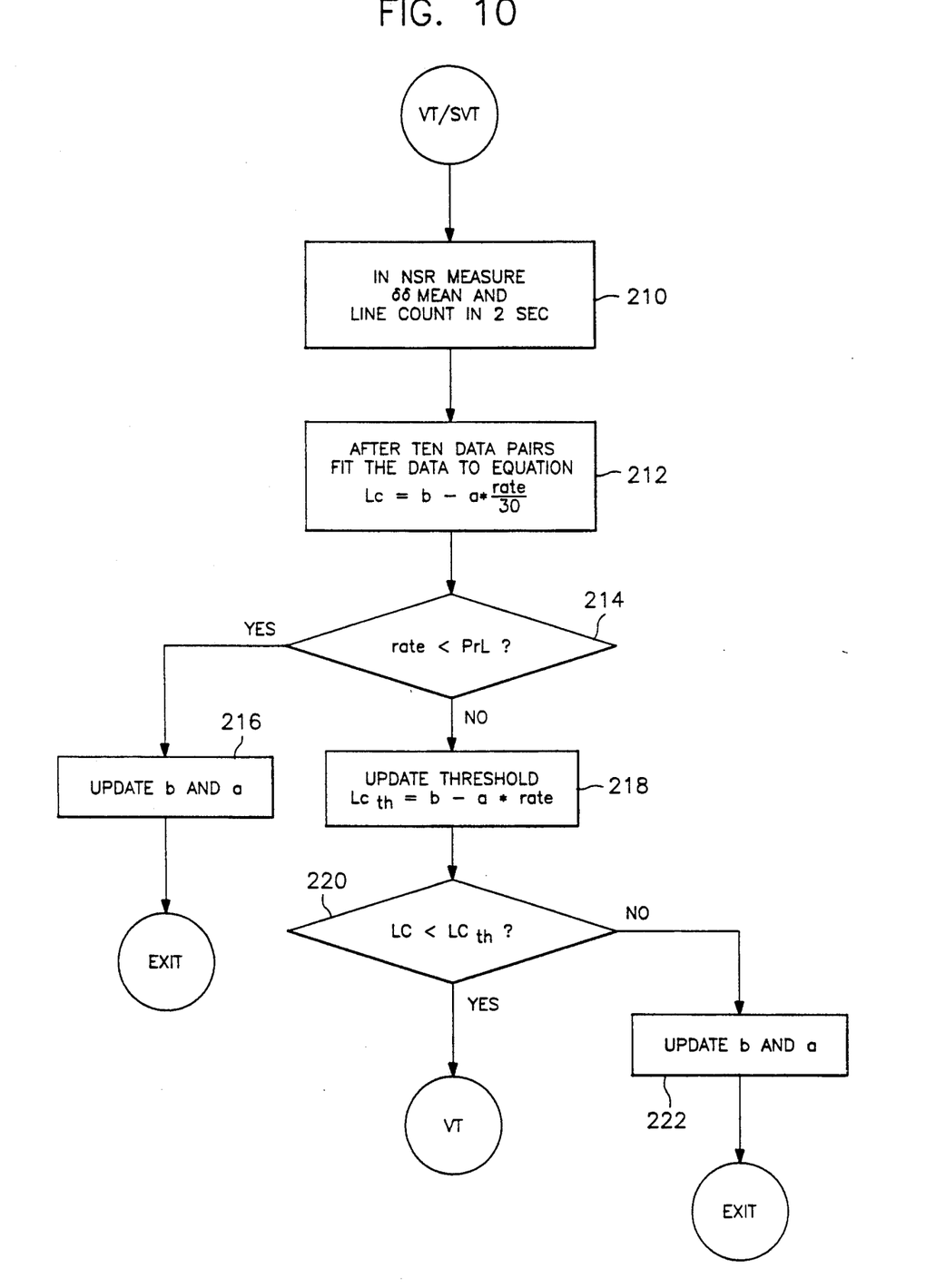
FIG. 10 is a flowchart illustrating the rate dependent thresholds for discriminating between supraventricular tachycardia and ventricular tachycardia.

FIG. 10 shows a flowchart for obtaining a rate dependent threshold used to discriminate between ventricular tachycardia and supraventricular tachycardia. In step 210, during normal sinus rhythm, (rate<prl, primary rate limit parameter programmable by the physician) every hour, 20 seconds of delta modulated data is taken. For each 2 second segment, both line-counts and average rate data are measured. In step 212, the data taken so far is fit into a regression equation LC=b−a*(rate/30), where b is the line-count of the flat line, which can be initialized to 256, and a is the line-count of a very high rate, which can be initialized to 22. For each hour, a new set of 10 pairs of LC verses rate data become available, updating the set of a and b coefficients. For any arrhythmia in the rate zone where VT verses SVT is in question, after 2 seconds of delta modulated ECG data has been taken, the average rate of the latest 4 R—R intervals can also be measured. In step 214, if the rate is less than the prl, then the line-count and average rate are used to update the regression coefficients a and b in step 216. If the rate is above prl, then a threshold can be generated according to the formula LC(TH)=b−a*(rate/30), as indicated in step 218. In step 220, if the current measured LC is less than the threshold, then the arrhythmia is declared to be VT. Otherwise, it will be declared as SVT and the line-count and rate data can be used to update the regression constant a and b for future use, as shown in step 222.

Figure 11:
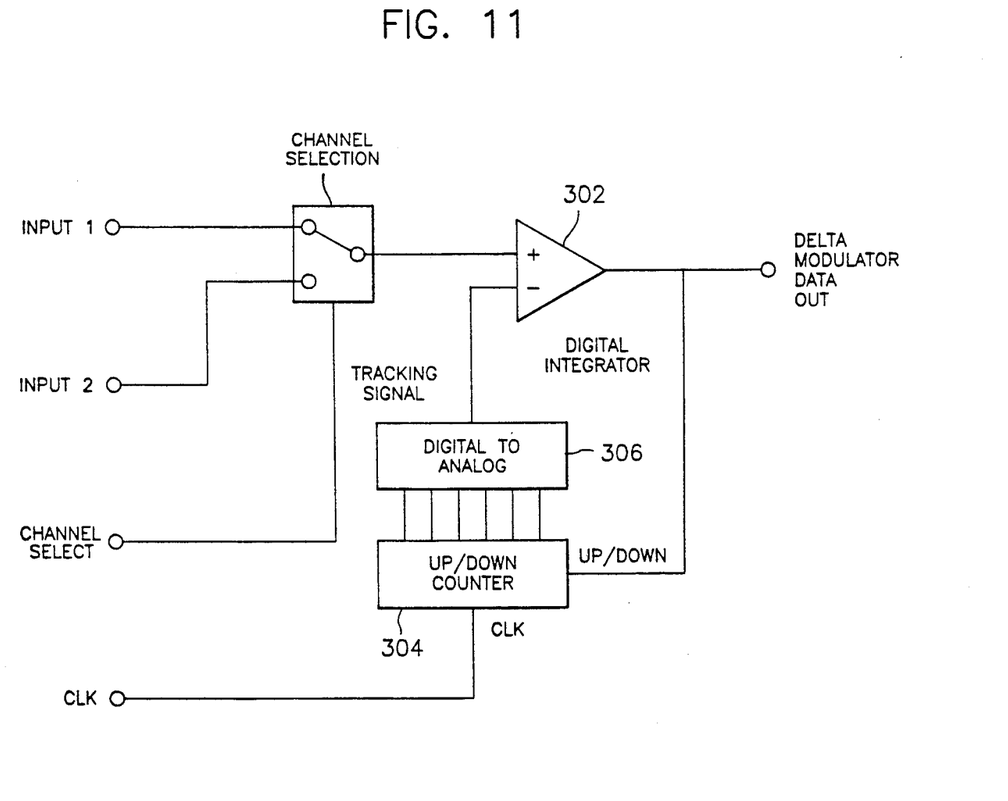
FIG. 11 is a block diagram of the delta modulator in accordance with the further principles of the present invention.

FIG. 11 is a block diagram of the delta modulator in accordance with the principles of the present invention. Delta modulated data is basically the error information between an incoming waveform (herein the ECG waveform at input 1 or input 2) and a tracking waveform signal which approximates the input. Delta modulated data can be thought of as instructions for reconstructing the input by stepping up or stepping down depending on the difference between the input signal and the tracking signal. In FIG. 11, input 1 and input 2 represent two channels which are supplied to an input multiplexer which selects which input channel will be digitized. One channel may be for a bipolar lead and the other may be for a patch. Only one of the two signals can be processed at any one time. This is accomplished by the channel select switch SW and in accordance with the channel select command signal applied thereto. The selected signal is applied to a comparator 302 which determines whether the input is greater or less than the inverse of the internal tracking signal. The tracking signal is generated by numerically integrating the binary state of the comparator 302. This is accomplished by feeding back the output of the comparator 302 to the up/down control of an up/down counter 304. The up/down counter 304 is incremented or decremented per the clock signal applied to its clock input, and the digital count from the counter 304 is applied to a digital-to-analog converter 306 which in turn generates the tracking signal for the comparator.

The data analyzed by the turning point morphology technique of the present invention must be normalized for the technique to function properly. To this end, the signal on the input 1 or 2 is modified by an automatic gain control (AGC) configuration such that normalized data will be generated after a few time constants.

Figure 12:
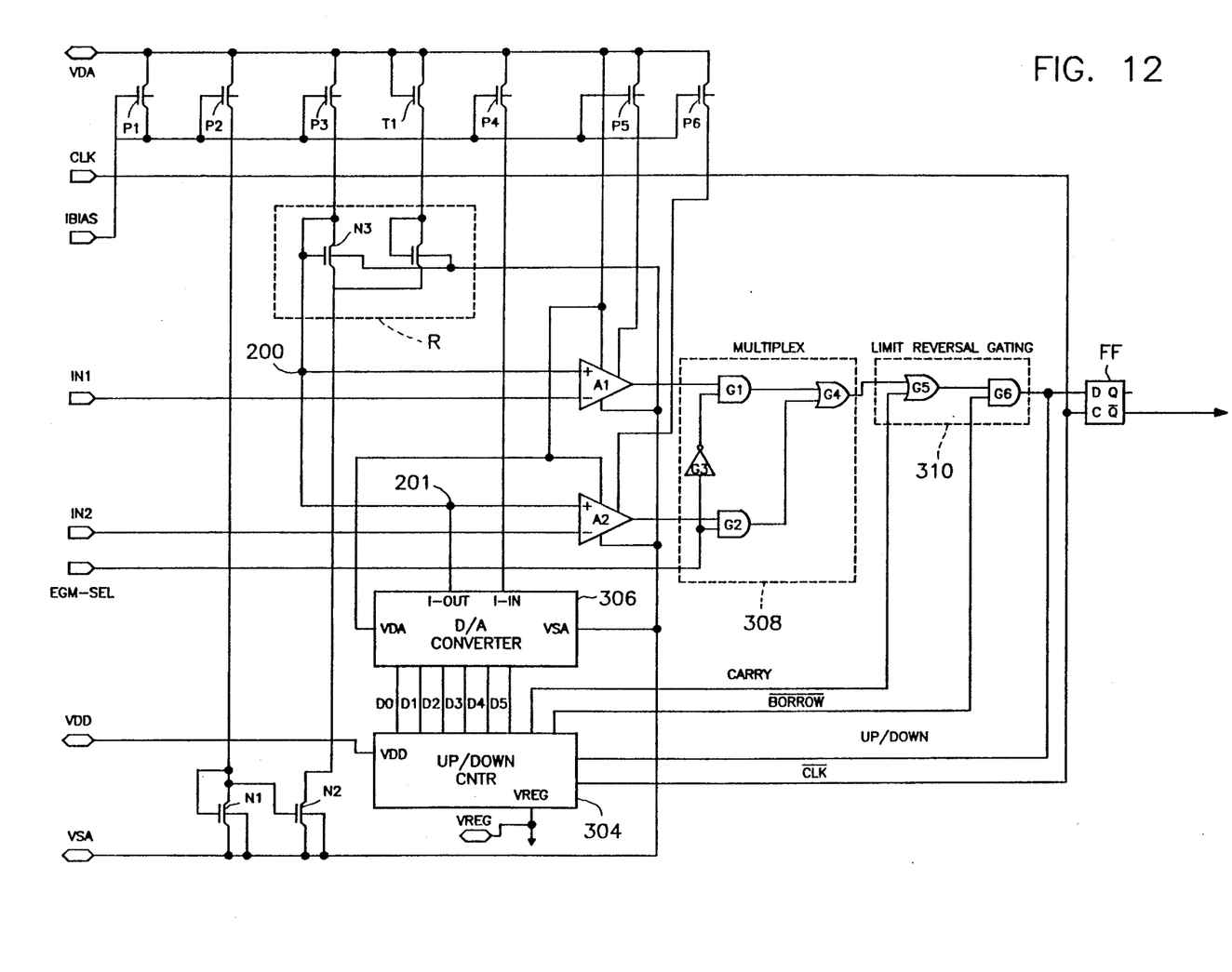
FIG. 12 is an electrical schematic of the delta modulator in accordance with the principles of the present invention.

An important feature of this delta modulator is that the integrator is formed by an up/down counter and D/A converter. Therefore, the integrator is completely drift free and, therefore, essentially a perfect integrator. Since drift is a problem with delta modulators, this simplifies the recovering of the waveform later because drift errors will not accumulate in the delta modulated data. FIG. 12 shows a circuit schematic for the integrated circuit implementation of the delta modulator. Table I that follows shows and describes the various inputs and signals applied to the integrated circuit:

TABLE I

| VDA | positive voltage rail |
|---|---|
| CLK | clock |
| IBIAS | current source (e.g., 50 na.) |
| IN1 | ECG input 1 |
| IN2 | ECG input 2 |
| EGM-SEL | input or channel select control line |
| VDD | mid-level voltage |
| VSA | negative voltage rail |

Transistors P1, P2, P3, P4, P5, P6, N1, and N2 provide current mirror rails (positive rails P1-P6 and negative rails N1-N2) to provide bias current for both comparators A1 and A2. Rather than having an analog switch before the comparator, two comparators are used for each input signal (IN1 and IN2); and a multiplexer 308, controlled by select signal EGM-SEL, selects one of the outputs of comparators A1 and A2. The current mirror rails provide bias currents for the comparators, the D/A converter 306 and the synthetic resistor circuit R that is defined by transistors N3 and N4 within the dashed box. The synthetic resistor circuit R and bipolar transistor T1 provide a loan for the current output of the D/A converter 306 at points 200 and 201 such that the result is a voltage numerically proportional to the binary word presented to the D/A converter 306 by the up/down counter 304. The voltage can vary at points 200 and 201 by ±170 mV around a point of 0.5 volts between VDD. This resistor/transistor network has a Thevenin equivalent voltage designed to be equal to the no signal DC value of the input signals (IN1 and IN2) or resting voltage of the sense amplifiers IN1 and IN2. This voltage is present when the up/down counter is reading a count of 32, which is at midscale of the counter. The comparators are connected to VDA for a positive voltage supply, to VSA as a negative voltage supply, and to P5 and P6 respectively for bias.

Another feature of the delta modulator is the overload behavior of the entire system. If the input ECG signal exceeds the dynamic range limit of the D/A converter, the modulator reverts to a toggled output data signal which is the equivalent of straight line clipping. With any other behavior, the recovered waveform could be severely distorted following overload. This over-limit protection is accomplished using the limit reversal gating circuit 310 comprised of OR gate G5 and AND gate G6. The Carry output from the up/down counter 304 is applied to one input of OR gate G5 whereas the complement of the Borrow signal is applied to AND gate G6.

If the input signal IN1 was very high (assuming IN is selected EGM-SEL), the output of D/A converter would have to be very low since the tracking signal follows the input signal. When the counter reaches its minimum count level, i.e., attempting to go below a zero count, the Not Borrow line would, therefore, go low. When the output of the AND gate goes low, since the Not up/down control is coupled to the output of the reversal circuitry, the counter counts up one at the next clock pulse. The Not Borrow line would go high because the counter counts up one. Since the output of the comparator would remain the same, the output of AND gate G6 then goes from low to high. The counter then counts down to its minimum value again. At the next clock pulse, the Not Borrow line goes low, indicating the minimum value and the cycle repeats. Therefore, the modulated output signal is toggled at the clock rate. A similar analysis applies for the over-limit control that is operated with the carry line and OR gate G6.

Flip-flop FF provides a storage for the output signal for one clock pulse in order to allow the signal to settle down and to provide a buffer between the output of the delta modulator and the modulator itself.

The foregoing description is intended by way of example only and is not intended to limit the present invention in any way except as set forth in the following claims.

I claim:

1. An arrhythmia detector for analyzing ECG signals obtained from a heart, said detector comprising:
   means for delta modulating an input ECG signal for obtaining a digital representation of said input ECG signal from a heart;
   means for periodically classifying said digital signal as representing no slope, positive slope, or negative slope segments of said input ECG signal and respectively generating a no slope, positive slope, or negative slope signal;

means for determining, based upon a sequence over a predetermined period of time of no slope, positive slope, and negative slope signals, the amount of time an isoelectric line segment is present in said input ECG signal over said predetermined period of time; and means for issuing a fibrillation signal when the amount of time an isoelectric line is present in said input ECG signal is less than a predetermined threshold.

2. The arrhythmia detector as claimed in claim 1, wherein said means for issuing generates said fibrillation signal when the amount of time an isoelectric line is present is less than said predetermined threshold during two out of three consecutive predetermined periods of time.

3. The arrhythmia detector as claimed in claim 1, wherein said means for delta modulating comprises an integrator, and said means for delta modulating outputs a digital signal based on the difference of said input ECG signal and a tracking signal provided by said integrator.

4. The arrhythmia detector as claimed in claim 1, wherein said means for periodically classifying includes means for generating a series of binary bits and storing said bits in a digital word, means for counting the number of zeros in said digital word, and means for generating said positive slope signal when said digital word has a greater number of zeros than ones, generating said negative slope signal when said digital word has a lesser number of zeros than ones, and generating said no slope signal when the number of zeros equals that of ones.

5. The arrhythmia detector as claimed in claim 1, wherein said means for determining generates an isoelectric line number corresponding to said amount of time an isoelectric line segment is present in said input ECG signal over said predetermined period of time, and wherein said means for determining includes a finite state machine means for mapping sequences of said no slope, positive slope, and negative slope signals to a finite number of states and certain transitions between states are assigned line count value increments corresponding to said isoelectric line number.

6. An arrhythmia detector for detecting at lest fibrillation and tachycardia by analyzing ECG signals obtained from a heart, said detector comprising:

means for digitizing an input ECG signal for obtaining a digital signal representation of said input ECG signal;

means for periodically classifying said digital signal representation as representing no slope, positive slope, or negative slope segments of said input ECG signal and respectively generating a no slope, positive slope, or negative slope signal;

means for determining, based upon a sequence over a predetermined period of time of no slope, positive slope, and negative slope signals the amount of time an isoelectric line segment is present in said input ECG signal over said predetermined period of time, and generating an isoelectric line number corresponding to said amount of time an isoelectric line segment is present in said input ECG signal over said predetermined period of time;

means for issuing and storing a preliminary fibrillation signal when the isoelectric line number fails to exceed a first threshold during said predetermined period of time such that if for any set of three consecutive predetermined periods of time at least two preliminary fibrillation signals are issued, a declaration of fibrillation is made; and means for issuing a tachycardia signal when said isoelectric line number fails to exceed a second threshold, said second threshold being greater than said first threshold during said predetermined period of time.

7. The arrhythmia detector of claim 6, wherein said means for digitizing is a delta modulator means for outputting a digital signal.

8. The arrhythmia detector of claim 6, wherein said means for periodically classifying said digital signal includes means for generating a series of binary bits and storing said bits in a digital word, means for counting the number of zeros in said digital word, and means for generating said positive slope signal when said digital word has a greater number of zeros than ones, generating said negative slope signal when said digital word has a lesser number of zeros than ones, and generating said no slope signal when the number of zeros equals that of ones.

9. The arrhythmia detector of claim 6, wherein said means for determining includes a finite state machine means for mapping sequences of said no slope, positive slope, and negative slope signals to a finite number of states and certain transitions between states are assigned line count values corresponding to said isoelectric line number.

10. The arrhythmia detector of claim 8, wherein said digital word has 8 binary bits representing an eight millisecond interval of said input ECG signal.

11. The arrhythmia detector of claim 6, wherein said predetermined period of time is two second and corresponds to 256 consecutive eight bit digital words representing consecutive eight millisecond intervals of said input ECG signal.

12. The arrhythmia detector as claimed in claim 6, including means for determining an average rate of the four last R—R intervals, wherein said means for issuing said tachycardia signal sets said second threshold according to a linear function of the heart rate as determined by said average rate of the four last R—R intervals within said predetermined period of time, wherein said linear function being determined by a linear regression from multiple data pairs collected from an extended period of time when the heart is in normal rhythm, said data pairs consisting of said isoelectric line number and said average rate of the last four R—R intervals within said predetermined period of time.

13. An arrhythmia detector for analyzing ECG signals obtained from a heart, said detector comprising:

means for digitizing an input ECG signal for obtaining a digital representation of said input ECG signal;

means for periodically classifying said digital signal as representing no slope, positive slope, and negative slope segments of said input ECG signal and respectively generating a no slope, positive slope, or negative slope signal;

means for determining, based upon a sequence over a predetermined period of time of no slope, positive slope, or negative slope signals, the amount of time an isoelectric line segment is present in said input ECG signal over said predetermined period of time; and means for issuing a fibrillation signal when the amount of time an isoelectric line is present in said input ECG signal is less than a first predetermined threshold.

14. The arrhythmia detector as claimed in claim 13, and further comprising means for issuing a tachycardia signal when the amount of time an isoelectric line segment is present fails to exceed a second threshold, said second threshold being greater than said first predetermined threshold during said predetermined period of time.

15. The arrhythmia detector as claimed in claim 14, including means for determining an average rate of the four last R—R intervals, wherein said means for issuing said tachycardia signal sets said second threshold according to a linear function of the heart rate as determined by said average rate of the four last R—R intervals within the predetermined period of time, wherein said linear function being determined by a linear regression from multiple data pairs collected from an extended period of time when the heart is in normal rhythm, said data pairs consisting of the amount of time an isoelectric line segment is present and average rate of the last four R—R intervals within said predetermined period of time.

16. An arrhythmia detector for detecting at least fibrillation by analyzing ECG signals obtained from a heart, said detector comprising:

means for digitizing an input ECG signal for obtaining a digital representation of said input ECG signal;

means for periodically classifying said digital signal as representing no slope, positive slope, and negative slope segments of said input ECG signal and respectively generating a no slope, positive slope, or negative slope signal;

means for determining, based upon a sequence over a predetermined period of time of no slope, positive slope, or negative slope signals the amount of time an isoelectric line segment is present in said input ECG signal over said predetermined period of time, and generating an isoelectric line number corresponding to said amount of time an isoelectric line segment is present in said input ECG signal over said predetermined period of time; and means for issuing and storing a preliminary fibrillation signal when the isoelectric line number fails to exceed a first threshold during said predetermined period of time such that if for any set of three consecutive predetermined periods of time at least two preliminary fibrillation signals are issued, a declaration of fibrillation is made.

17. The arrhythmia detector as claimed in claim 16, further comprising means for issuing a tachycardia signal when said isoelectric line number fails to exceed a second threshold, said second threshold being greater than said first threshold during said predetermined period of time.

18. The arrhythmia detector as claimed in claim 17, including means for determining an average rate of the four last R—R intervals, wherein said means for issuing said tachycardia signals sets said second threshold according to a linear function of the heart rate as determined by said average rate of the four last R—R intervals within the predetermined period of time, wherein said linear function being determined by a linear regression from multiple data pairs collected from an extended period of time when the heart is in normal rhythm, said data pairs consisting of said isoelectric line number and said average rate of the last R—R intervals within said predetermined period of time.

* * * * *